United States Patent
Wright et al.

[11] Patent Number: 5,750,468
[45] Date of Patent: May 12, 1998

[54] GLYPHOSATE FORMULATIONS CONTAINING ETHERAMINE SURFACTANTS

[75] Inventors: Daniel R. Wright, St. Louis; Ronald J. Brinker, Ellisville; Joseph J. Sandbrink, St. Louis; Al S. Wideman, St. Louis County, all of Mo.

[73] Assignee: Monsanto Company, St. Louis, Mo.

[21] Appl. No.: 599,363

[22] Filed: Mar. 15, 1996

Related U.S. Application Data

[63] Continuation-in-part of Ser. No. 419,299, Apr. 10, 1995, abandoned.

[51] Int. Cl.$^6$ .................... A01N 25/30; A01N 57/02
[52] U.S. Cl. ........................................... 504/206
[58] Field of Search ............................. 504/206

[56] References Cited

U.S. PATENT DOCUMENTS 5,317,003  5/1994  Kassebaum et al. ............... 504/116

FOREIGN PATENT DOCUMENTS

| | | |
|---|---|---|
| 0274369 | 7/1988 | European Pat. Off. . |
| 0290416 | 11/1988 | European Pat. Off. . |
| 1588079 | 4/1981 | United Kingdom . |
| 95/33379 | 12/1995 | WIPO . |

OTHER PUBLICATIONS

McWhorter, C. G. "The Physiologocal Effects of Adjuvants on Plants" Chapter 6 in S. O. Duke, ed., *Weed Physiology: vol. II; Herbicide Physiology*, CRC Press, Boca Raton, Florida, 141–158, 1985.
Wyrill and Burnsid, Weed Science, vol. 25 (1977), pp. 275–287.
Brochure: Tomah Products, Inc., dated Aug. 22, 1994, "Ethoxylated Amines".
Brochure: Tomah Products, Inc., dated Sep. 1, 1994, "Quaternaries".

*Primary Examiner*—S. Mark Clardy
*Attorney, Agent, or Firm*—Arnold, White & Durkee

[57] ABSTRACT

Herbicidal compositions are provided comprising glyphosate or a salt thereof and an etheramine surfactant having the representative chemical structure (a)

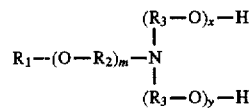

wherein $R_1$ is a straight or branched chain $C_6$ to about $C_{22}$ alkyl, aryl or alkylaryl group, m is an average number from 1 to about 10, $R_2$ in each of the m ($O-R_2$) groups is independently $C_1-C_4$ alkylene, $R_3$ groups are independently $C_1-C_4$ alkylene, and x and y are average numbers such that x+y is in the range from 2 to about 60; or (b)

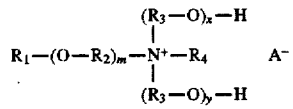

wherein $R_1$ is a straight or branched chain $C_6$ to about $C_{22}$ alkyl, aryl or alkylaryl group, m is an average number from 1 to about 10, $R_2$ in each of the m ($O-R_2$) groups is independently $C_1-C_4$ alkylene, $R_3$ groups are independently $C_1-C_4$ alkylene, $R_4$ is $C_1-C_4$ alkyl, x and y are average numbers such that x+y is in the range from 0 to about 60, and $A^-$ is an agriculturally acceptable anion; or (c)

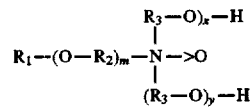

wherein $R_1$ is a straight or branched chain $C_6$ to about $C_{22}$ alkyl, aryl or alkylaryl group, m is an average number from 1 to about 10, $R_2$ in each of the m ($O-R_2$) groups is independently $C_1-C_4$ alkylene, $R_3$ groups are independently $C_1-C_4$ alkylene, and x and y are average numbers such that x+y is in the range from 2 to about 60.

61 Claims, No Drawings

GLYPHOSATE FORMULATIONS CONTAINING ETHERAMINE SURFACTANTS

CROSS-REFERENCE TO RELATED APPLICATION

This is a continuation-in-part of application Ser. No. 08/419,299 filed Apr. 10, 1995, abandoned.

FIELD OF THE INVENTION

Novel agriculturally acceptable formulations of the herbicide N-phosphonomethylglycine (glyphosate) comprising tertiary or quaternary etheramine or etheramine oxide surfactants are provided.

BACKGROUND OF THE INVENTION

Glyphosate is well known as a highly effective and commercially important herbicide useful for combating the presence of a wide variety of unwanted vegetation, including agricultural weeds. Glyphosate is conventionally applied as a formulated product dissolved in water to the foliage of annual and perennial grasses and broadleaf plants and the like, is taken up over a period of time into the leaves, and thereafter translocates throughout the plant.

Usually, glyphosate is formulated in commercial compositions in the form of a water-soluble salt. Salts in commercial use include the ammonium salt, alkylamine salts, such as the isopropylamine salt, alkali metal salts, such as the sodium salt, and the trimethylsulfonium salt. However, formulations of glyphosate in its acid form are also used. Typical glyphosate salt formulations include aqueous concentrates, requiring simple dilution and distribution in water for application by the end-user, and water-soluble or water-dispersible dry formulations, especially granules, requiring dissolution or dispersion in water prior to application.

Under most application conditions, the herbicidal efficacy of glyphosate can be significantly enhanced by including one or more surfactants in the composition to be applied. It is believed that such surfactants act partly by facilitating the penetration of glyphosate, a relatively hydrophilic compound, through the rather hydrophobic cuticle which normally covers the external above-ground surfaces of higher plants.

Wyrill and Burnside, Weed Science, Vol. 25 (1977), pp. 275-287, conducted a wide-ranging study of different classes of surfactants as agents for enhancing the herbicidal activity of glyphosate, applied as the isopropylamine salt. They demonstrated that the choice of surfactant has a pronounced effect on the herbicidal performance of a glyphosate formulation, but beyond showing a general tendency for surfactants having high values of hydrophile-lipophile balance (HLB) to be more efficacious than surfactants of the same class having low HLB values, they did not observe any predictive relationship between efficacy and surfactant chemical class. Some of the most effective surfactants identified in the Wyrill and Burnside study were ethoxylated tertiary and quaternary alkylamines.

Commercial formulations of glyphosate have frequently used ethoxylated tertiary alkylamine surfactants, for example an ethoxylated tallowamine having an average of about 15 moles of ethylene oxide (EO) per mole of tallowamine. Monsanto Company of St. Louis, Mo. has for many years sold, under the trademark Roundup® herbicide, glyphosate formulations containing various concentrations of such an ethoxylated tallowamine surfactant.

European Patent No. 0 290 416 to Forbes et al. discloses compositions of glyphosate salts comprising ethoxylated tertiary alkylamine surfactants having less than 15 moles of EO. For example a composition is disclosed comprising the isopropylamine salt of glyphosate and an ethoxylated cocoamine surfactant having an average of 5 moles of EO. It is taught by Forbes et al. that certain herbicidal efficacy advantages are obtainable with such compositions by comparison with compositions where the EO level in the surfactant is around 15 moles.

European Patent No. 0 274 369 to Sato et al. discloses glyphosate compositions comprising ethoxylated quaternary alkylamine surfactants. Several examples are shown wherein the surfactant is an ethoxylated N-methyl cocoammonium chloride surfactant having 2 moles of EO.

A drawback of ethoxylated tertiary alkylamine surfactants of prior art is that when included in concentrate formulations at levels consistent with good herbicidal performance, they tend to be irritant to eyes. In some, but not all, cases, eye irritancy can be reduced by converting the tertiary alkylamine to the corresponding quaternary (N-methyl) alkylamine. U.S. Pat. No. 5,317,003 to Kassebaum discloses that a glyphosate composition containing as the surfactant an ethoxylated N-methyl cocoammonium chloride surfactant having 15 moles of EO is less irritant to eyes than an otherwise identical composition wherein the surfactant is an ethoxylated tertiary cocoamine surfactant having 15 moles of EO.

An alternative solution to the eye irritancy problem is suggested in U.S. Pat. No. 5,118,444 to Nguyen, wherein ethoxylated tertiary alkylamine surfactants are converted to their N-oxides. Examples are shown of glyphosate compositions wherein the surfactant is an ethoxylated tallowamine oxide surfactant having 10, 15 or 20 moles of EO.

A further drawback of ethoxylated tertiary alkylamine surfactants of the prior art is that when water is added to them, they tend to form a stiff gel which adds to the complexity and expense of manufacturing formulations containing such surfactants, by making it difficult to clean vessels and pipes. In practice, this problem is ameliorated by adding an anti-gelling agent, such as polyethylene glycol, to the surfactant.

Never previously disclosed as components of concentrate glyphosate formulations are alkoxylated tertiary or quaternary etheramine or etheramine oxide surfactants. United Kingdom Patent No. 1,588,079 to Texaco Development Corporation discloses examples of ethoxylated alkyloxyisopropylamine and alkylpoly(isopropyl)amine surfactants and methods of preparing them, and suggests they are useful as detergents, dispersants, wetting agents and emulsifiers. Surfactants disclosed have the representative chemical structure

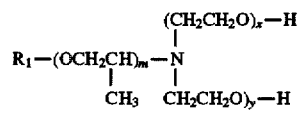

wherein $R_1$ is $C_8$–$C_{18}$ alkyl, m is a number from 1 to 5, and x and y are average numbers such that x+y is in the range from 2 to 20.

Tomah Products, Inc. of Milton, Wis. in a brochure titled "Ethoxylated Amines", dated Aug. 22, 1994, disclose, together with a series of ethoxylated tertiary alkylamines, a number of ethoxylated tertiary etheramine surfactants having the representative chemical structure

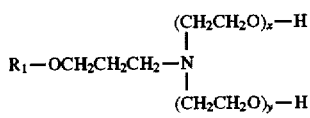

wherein $R_1$ is $C_{10}$–$C_{26}$ alkyl and x and y are average numbers such that x+y is in the range from 2 to 15. Suggested uses of the Tomah ethoxylated amines include "agricultural adjuvants", a well-known application of the ethoxylated tertiary alkylamines listed. No suggestion is made that the ethoxylated tertiary etheramines included in the list would have advantages over the ethoxylated tertiary alkylamines as agricultural adjuvants, nor is there any teaching relevant to the making of concentrate glyphosate compositions with ethoxylated tertiary etheramines.

Another brochure from Tomah Products titled "Quaternaries", dated Sep. 1, 1994, includes in a list of quaternary amine surfactants a number of ethoxylated quaternary etheramines having the representative chemical structure

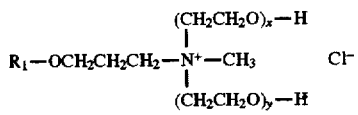

wherein $R_1$ is an aliphatic group exemplified by isodecyl or isotridecyl and x+y is 2. The list of suggested uses for Tomah's quaternaries does not include agricultural adjuvants.

Another brochure from Tomah Products titled "AO-14-2", dated Aug. 24, 1994, discloses an ethoxylated etheramine oxide which can be deduced to have the representative chemical structure

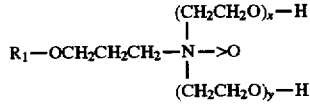

wherein $R_1$ is an aliphatic group exemplified by isodecyl and x+y is 2. The list of suggested uses for AO-14-2 does not include agricultural adjuvants.

It is an object of the present invention to provide novel compositions of glyphosate herbicide containing an etheramine surfactant which imparts good herbicidal efficacy, yet having low irritancy to eyes.

It is a further object of the present invention to provide the commercial formulator of glyphosate with an alternative to ethoxylated alkylamine surfactants that (1) allows elimination or substantial reduction of the need for the use of an anti-gelling agent, (2) is soluble in aqueous formulations having higher glyphosate acid equivalent loadings than prior art formulations having comparable efficacy, and (3) provides herbicidal efficacy superior to that obtainable with comparable amounts of said ethoxylated alkylamine surfactants having similar degrees of ethoxylation.

It is a further object of the present invention to provide concentrate liquid and dry formulations of glyphosate with an etheramine surfactant having good storage stability.

These and other objectives are satisfied by the compositions disclosed herein.

SUMMARY OF THE INVENTION

There are provided new herbicidal compositions comprising glyphosate or a salt thereof and an etheramine surfactant, defined as an amine surfactant in which the hydrophobe is connected to the amine group via a series of up to about 10 oxyalkylene groups.

Specifically, the etheramine surfactant may be a tertiary amine having the representative chemical structure

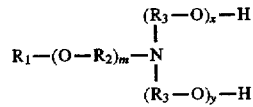

wherein $R_1$ is a straight or branched chain $C_6$ to about $C_{22}$ alkyl, aryl or alkylaryl group, m is an average number from 1 to about 10, $R_2$ in each of the m (O—$R_2$) groups is independently $C_1$–$C_4$ alkylene, $R_3$ groups are independently $C_1$–$C_4$ alkylene, and x and y are average numbers such that x+y is in the range from 2 to about 60.

Alternatively, the etheramine surfactant may be a quaternary amine having the representative chemical structure

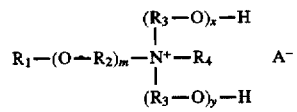

wherein $R_1$ is a straight or branched chain $C_6$ to about $C_{22}$ alkyl, aryl or alkylaryl group, m is an average number from 1 to about 10, $R_2$ in each of the m (O—$R_2$) groups is independently $C_1$–$C_4$ alkylene, $R_3$ groups are independently $C_1$–$C_4$ alkylene, $R_4$ is $C_1$–$C_4$ alkyl, x and y are average numbers such that x+y is in the range from 0 to about 60, and $A^-$ is an agriculturally acceptable anion.

As a third possibility, the etheramine surfactant may be an amine oxide having the representative chemical structure

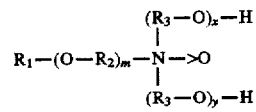

wherein $R_1$ is a straight or branched chain $C_6$ to about $C_{22}$ alkyl, aryl or alkylaryl group, m is an average number from 1 to about 10, $R_2$ in each of the m (O—$R_2$) groups is independently $C_1$–$C_4$ alkylene, $R_3$ groups are independently $C_1$–$C_4$ alkylene, and x and y are average numbers such that x+y is in the range from 2 to about 60.

Compositions of the invention may be prepared on site by the end-user shortly before application to the foliage of vegetation to be killed or controlled, by mixing in aqueous solution a glyphosate containing composition and a composition comprising a surfactant having a chemical structure encompassed by those represented immediately above. Such compositions of the invention are referred to herein as "tank-mix" compositions.

Alternatively, compositions of the invention may be provided to the end-user already formulated, either at the desired dilution for application ("ready to use" compositions) or requiring dilution, dispersion or dissolution in water by the end-user ("concentrate" compositions). Such preformulated compositions of the invention are storage-stable and may be liquid or dry.

A method of use of compositions of the invention to kill or control weeds or other unwanted vegetation is also provided.

DETAILED DESCRIPTION OF THE INVENTION

Compositions of the invention may contain glyphosate in its acid form. However, because of the relatively low solubility of glyphosate acid in water, more soluble salts of glyphosate are generally preferred. As in commercial compositions of prior art, an especially preferred salt for aqueous compositions of the invention is the isopropylamine salt of glyphosate, while an especially preferred salt for dry compositions of the invention is the ammonium salt. Many other salts may be used either in aqueous or in dry formulations, including but not restricted to alkylamine, such as dimethylamine and n-propylamine, alkanolamine, such as monoethanolamine, alkylsulfonium, such as trimethylsulfonium, and alkali metal, such as sodium and potassium, salts of glyphosate. Regardless of whether acid or a salt is used, it is generally preferred to refer to the amount of glyphosate applied or contained in a formulation in terms of glyphosate acid equivalent, conventionally abbreviated as "a.e.".

Tank-mix and ready to use compositions of the invention are aqueous solutions comprising from about 1 to about 50 g glyphosate a.e./l, occasionally more. A preferred range for tank-mix and ready to use compositions is from about 5 to about 20 g a.e./l.

Concentrate compositions of the invention may be aqueous solutions comprising from about 50 to about 500 g glyphosate a.e./l or more, preferably from about 200 to about 500 g a.e./l and most preferably from about 350 to about 500 g a.e./l. An example of an especially preferred aqueous concentrate composition of the invention contains the isopropylamine salt of glyphosate at about 360 g a.e./l, the same level as is present in commercial compositions being sold as Roundup® herbicide by Monsanto Company.

A surprising advantage of aqueous compositions of the invention over prior art compositions is that the glyphosate concentration can be increased to very high levels, for example from about 450 to about 500 g a.e./l, yet the surfactant concentration is still adequate to give excellent herbicidal performance without the end-user requiring to add more surfactant in the spray tank. Many such highly concentrated compositions have remarkably good storage stability under a wide range of temperature conditions.

Alternatively, concentrate compositions of the invention may be dry formulations, presented for example in the form of powders, pellets, tablets or, preferably, granules, to be dispersed or dissolved in water prior to use. Typically no water-insoluble ingredients are present at substantial levels in such compositions and the formulations are therefore fully water-soluble. Dry water-soluble or water-dispersible compositions of the invention comprise from about 20% to about 80% weight/weight glyphosate a.e., preferably from about 50% to about 76%, and most preferably from about 60% to about 72%. An example of an especially preferred water-soluble granular composition of the invention contains the ammonium salt of glyphosate at about 72% weight/weight, the same level as is present in commercial compositions being sold as Scout® herbicide by Monsanto Company.

In dry compositions of the invention glyphosate may itself provide the support for other formulation ingredients, or there may additionally be present one or more inert ingredients providing such support. An example of an inert support that may be used is ammonium sulfate. The term "dry" as used herein does not imply that dry compositions are totally free of water; typically dry compositions of the invention comprise from about 0.5 to about 5 percent by weight, preferably less than about 1 percent by weight water.

Dry water-soluble or water-dispersible granular formulations of the invention can be made by any process known in the art, including but not restricted to spray drying, fluid-bed agglomeration, pan granulation, or extrusion. In dry formulations, glyphosate may be present as a salt, for example the sodium or ammonium salt, or as the acid. Formulations containing glyphosate acid may optionally contain an acid acceptor such as an ammonium or alkali metal carbonate or bicarbonate, ammonium dihydrogen phosphate or the like, so that upon dissolution or dispersion in water by the end user a water soluble salt of glyphosate is produced.

What distinguishes compositions of the invention from all previously described glyphosate compositions is the presence therein of an alkoxylated tertiary or an alkoxylated or non-alkoxylated quaternary etheramine or an alkoxylated etheramine oxide surfactant having the representative chemical structure (a)

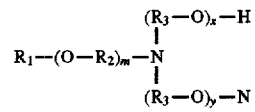

wherein $R_1$ is a straight or branched chain $C_6$ to about $C_{22}$ alkyl, aryl or alkylaryl group, m is an average number from 1 to about 10, $R_2$ in each of the m (O—$R_2$) groups is independently $C_1$–$C_4$ alkylene, $R_3$ groups are independently $C_1$–$C_4$ alkylene, and x and y are average numbers such that x+y is in the range from 2 to about 60; or (b)

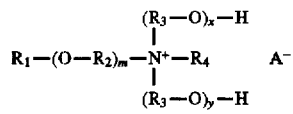

wherein $R_1$ is a straight or branched chain $C_6$ to about $C_{22}$ alkyl, aryl or alkylaryl group, m is an average number from 1 to about 10, $R_2$ in each of the m (O—$R_2$) groups is independently $C_1$–$C_4$ alkylene, $R_3$ groups are independently $C_1$–$C_4$ alkylene, $R_4$ is $C_1$–$C_4$ alkyl, x and y are average numbers such that x+y is in the range from 0 to about 60, and $A^-$ is an agriculturally acceptable anion; or (c)

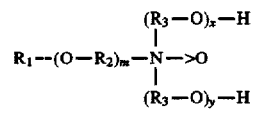

wherein $R_1$ is a straight or branched chain $C_6$ to about $C_{22}$ alkyl, aryl or alkylaryl group, m is an average number from 1 to about 10, $R_2$ in each of the m (O—$R_2$) groups is independently $C_1$–$C_4$ alkylene, $R_3$ groups are independently $C_1$–$C_4$ alkylene, and x and y are average numbers such that x+y is in the range from 2 to about 60.

Alkylamine or alkylamine oxide surfactants in glyphosate compositions of prior art have no (O—$R_2$) groups, in other words m=0. We have found that surprisingly improved properties can be imparted to glyphosate compositions when from 1 to about 10 (O—$R_2$) groups are inserted in the surfactant structure between the $R_1$ group and the nitrogen atom.

Aryl groups, if present in $R_1$, have 5–7, preferably 6, carbon atoms and may or may not be substituted with moieties. The alkyl portion in any alkylaryl group comprising $R_1$ has 1–16 carbon atoms. An example of such an alkylaryl group is alkylphenyl, for example nonylphenyl.

However, in preferred surfactants of the invention $R_1$ is a straight or branched chain alkyl group having about 8 to about 18, for example about 10–15, carbon atoms, and are derived from the corresponding alcohol. For example, the alkyl group may be of natural derivation, such as from coconut or tallow, or may be derived from a synthetic alcohol such as isodecyl, isotridecyl, linear $C_{12}$–$C_{14}$ or octadecyl alcohols.

The $R_2$ substituent closest to the nitrogen atom (the proximal $R_2$ group) is in preferred examples a linear propylene ($-CH_2CH_2CH_2-$), isopropylene ($-CH_2CH(CH_3)-$) or ethylene ($-CH_2CH_2-$) group. Preferred examples where the proximal $R_2$ group is linear propylene have m=1. Where the proximal $R_2$ group is isopropylene or ethylene, m is preferably in the range from 1 to 5, most preferably from 2 to 3, and all $R_2$ groups are preferably the same.

$R_3$ substituents in preferred examples are independently selected from isopropylene and ethylene. In especially preferred examples all $R_3$ groups are ethylene. In tertiary etheramines and etheramine oxides of the invention it is preferred that x+y is in the range from 2 to about 20. In quaternary etheramines of the invention it is preferred that x+y is in the range from 0 to about 20. A particularly preferred range for x+y in tertiary and quaternary etheramines and etheramine oxides of the invention is from 2 to about 10, more particularly from 2 to about 5.

In quaternary etheramines of the invention $R_4$ is preferably methyl and $A^-$ is preferably a halide, for example chloride or bromide, a phosphate or a sulfate ion, or alternatively may be a glyphosate ion or may be contributed by an anionic surfactant included with the etheramine in the formulation. It will be recognized by those skilled in the art that at low pH, such as may well exist in a glyphosate formulation, tertiary etheramines will most likely be protonated at the nitrogen atom and may be associated with a counterion; in such cases the tertiary etheramine can be represented by the chemical structure shown above for a quaternary etheramine, except that $R_4$ is hydrogen. The counterion $A^-$ in a low pH glyphosate formulation comprising a tertiary etheramine is most likely glyphosate itself.

One especially preferred surfactant useful in compositions of the invention is a tertiary etheramine having $R_1$=$C_{12}$–$C_{14}$ alkyl, $R_2$=isopropylene, m=2, $R_3$=ethylene and x+y=5.

Another especially preferred surfactant useful in compositions of the invention is a tertiary etheramine having $R_1$=$C_{12}$–$C_{14}$ alkyl, $R_2$=ethylene, m=3, $R_3$=ethylene and x+y=5.

Two other especially preferred surfactants useful in compositions of the invention are tertiary etheramines having $R_1$=isodecyl, $R_2$=linear propylene, m=1, $R_3$ ethylene and x+y=2 or 5 respectively.

Another series of especially preferred surfactants useful in compositions of the invention is a tertiary etheramine having $R_1$=coco alkyl, $R_2$=linear propylene, m=1, $R_3$=ethylene and x+y=a number in the range from 2 to 10.

Two other especially preferred surfactants useful in compositions of the invention are tertiary etheramines having $R_1$=isotridecyl, $R_2$=linear propylene, m=1, $R_3$=ethylene and x+y=2 or 5 respectively.

Two other especially preferred surfactants useful in compositions of the invention are quaternary etheramines having $R_1$=isodecyl or isotridecyl respectively, $R_2$=linear propylene, $R_3$=ethylene, $R_4$=methyl, m=1 and x+y=2.

Any convenient and effective herbicidal activity enhancing amount of the etheramine surfactant can be used in compositions of the invention. In tank-mix and ready to use formulations very high levels of surfactant are achievable, for example up to 5% weight/volume or even higher, but for reasons of economy it will be more normal to use a concentration in the range from about 0.125% to about 2% weight/volume. One of ordinary skill in the art will be able to determine from tests on different plant species an appropriate level of etheramine surfactant to include for any particular glyphosate application.

In concentrate liquid or dry compositions of the invention, the etheramine surfactant is preferably included at a weight/weight ratio to glyphosate a.e. in the range from about 1:20 to about 1:1, most preferably from about 1:10 to about 1:2, for example about 1:6.

Long-term storage stability is an important commercial attribute of concentrate formulations. In the case of aqueous concentrate formulations of glyphosate salts, it is particularly important that surfactants in the formulation do not separate from the other ingredients as a distinct phase. Many aqueous concentrates made with surfactants of prior art show a tendency for phase separation at high temperatures. It is a feature of the etheramine surfactants herein disclosed that they show good compatibility with glyphosate salts, particularly the isopropylamine salt, as evidenced by relatively high cloud points even in aqueous solutions having high glyphosate concentrations. In general for most applications, a cloud point higher than about 50° C. is desirable.

In addition to glyphosate or a salt thereof and the etheramine surfactant, any of a variety of further ingredients or adjuvants may be included in formulations of the present invention, as long as such added materials are not significantly antagonistic to the glyphosate herbicidal activity. Examples of such added materials illustratively include anti-gelling agents, antifreezes, thickeners, dyes, antimicrobial preservatives or additives to further enhance herbicidal activity, such as ammonium sulfate or fatty acids.

A second surfactant of a class other than etheramines, for example a primary or secondary alcohol ethoxylate, an alkyl ester of sucrose or sorbitan, or an alkyl polyglucoside, may also be included. When such a second surfactant is present, it is preferable that the weight/weight ratio of etheramine to the second surfactant is greater than about 1:1, most preferably greater than about 2:1, for example around 4:1.

Preferably when a second surfactant is included in a highly concentrated glyphosate formulation of the invention, for example one containing about 450 to about 500 g a.e./l, the etheramine surfactant comprises at least about 75% by weight of the total surfactant present.

Mixtures of glyphosate with other herbicides are also within the scope of the present invention if an etheramine surfactant is included in the formulation. Examples of such other herbicides include bialaphos, glufosinate, 2,4-D, MCPA, dicamba, diphenylethers, imidazolinones and sulfonylureas.

Methods of use of glyphosate formulations are well known to those of skill in the art. Aqueous concentrate formulations of the invention are diluted in an appropriate volume of water and applied, for example by spraying, to the weeds or other unwanted vegetation to be killed or controlled. Dry concentrate formulations of the invention are dissolved or dispersed in an appropriate volume of water and applied in the same way. For most purposes, compositions of the invention are applied at glyphosate a.e. rates in the range from about 0.1 to about 5 kg/ha, occasionally more. Typical glyphosate a.e. rates for control of annual and perennial grasses and broadleaves are in the range from about 0.3 to about 1.5 kg/ha. Compositions of the invention may be applied in any convenient volume of water, most typically in the range from about 50 to about 1000 l/ha.

9

The present invention is illustrated by but not limited to the following Examples.

EXAMPLES

Cloud point was determined for certain liquid compositions of the Examples as follows. A sample of the composition in a test tube was heated in a water bath until it became cloudy. The test tube was then removed from the water bath and the sample stirred with a thermometer until it became clear. The temperature at which the sample became clear was recorded as the cloud point of the composition.

Percentages expressed as "%" in the following Examples are by weight/weight unless otherwise indicated.

Example 1

The surfactant used in Example 1 is a tertiary etheramine having the chemical structure represented above in which $R_1$ is $C_{12}$–$C_{14}$ alkyl, m is 3, x+y is 5 and $R_2$ and $R_3$ are each ethylene.

The aqueous concentrate composition of Example 1 was prepared by mixing the following ingredients in the order given:

(1) aqueous solution of glyphosate isopropylamine salt containing 46% glyphosate a.e., 67.4 g.

(2) surfactant as defined above, 10.0 g.

(3) deionized water, 22.6 g.

The composition can be calculated to contain 31% glyphosate a.e. and 10% surfactant. Specific gravity of the composition at 20/15.6° C. was determined to be 1.1628. Cloud point of the composition was >90° C.

Example 2

The surfactant used in Example 2 is the same as that used in Example 1. The aqueous concentrate composition of Example 2 was prepared by mixing the following ingredients in the order given:

(1) aqueous solution of glyphosate isopropylamine salt containing 46% glyphosate a.e., 1348 g.

(2) surfactant as defined above, 110 g.

(3) deionized water, 542 g.

The composition can be calculated to contain 31% glyphosate a.e. and 5.5% surfactant. Specific gravity of the composition at 20/15.6° C. was determined to be 1.1630. Cloud point of the composition was >90° C.

The composition of Example 2 was submitted for eye irritation testing according to the standard procedure prescribed in US Environmental Protection Agency (EPA) Publication 540/9-82-025, November 1982, entitled Pesticidal Assessment Guidelines, Subdivision F, Hazard Evaluation: Human and Domestic Animals. The study was conducted in compliance with EPA Good Laboratory Practice (GLP) standards. Results were obtained placing the composition in toxicity category III, indicating low irritancy to eyes.

Example 3

The surfactant used in Example 3 is a tertiary etheramine having the chemical structure represented above in which $R_1$ is $C_{12}$–$C_{14}$ alkyl, m is 2, x+y is 5, $R_2$ is isopropylene and $R_3$ is ethylene.

The aqueous concentrate composition of Example 3 was prepared by mixing the following ingredients in the order given:

(1) aqueous solution of glyphosate isopropylamine salt containing 46% glyphosate a.e., 1348 g.

(2) surfactant as defined above, 200 g.

(3) deionized water, 452 g.

The composition can be calculated to contain 31% glyphosate a.e. and 10% surfactant. Specific gravity of the composition at 20/15.6° C. was determined to be 1.1618. Cloud point of the composition was >90° C.

Example 4

The surfactant used in Example 4 is the same as that used in Example 3. The aqueous concentrate composition of Example 4 was prepared by mixing the following ingredients in the order given:

(1) aqueous solution of glyphosate isopropylamine salt containing 46% glyphosate a.e., 1348 g.

(2) surfactant as defined above, 110 g.

(3) deionized water, 542 g.

The composition can be calculated to contain 31% glyphosate a.e. and 5.5% surfactant. Specific gravity of the composition at 20/15.6° C. was determined to be 1.1617. Cloud point of the composition was >90° C.

The composition of Example 4 was submitted for eye irritation testing according to the standard procedure prescribed in EPA Publication 540/9-82-025, November 1982 cited above. The study was conducted in compliance with GLP standards. Results were obtained placing the composition in in toxicity category III, indicating low irritancy to eyes.

Examples 5–7

The surfactants used in Examples 5–7 are tertiary etheramines having the chemical structure represented above in which $R_1$ is $C_{12}$–$C_{14}$ alkyl, m is 3 and $R_2$ and $R_3$ are each ethylene. The value of x+y is varied as shown in the table below.

Aqueous concentrate compositions containing 31% glyphosate a.e. in the form of the isopropylamine salt and 11% surfactant were prepared by a procedure similar to that of Examples 1–4. Cloud point of each composition was determined as shown in the table below.

| Example | x + y | Cloud point (°C.) |
|---|---|---|
| 5 | 5 | >95 |
| 6 | 10 | 81 |
| 7 | 15 | 66 |

Examples 8–11

The surfactants used in Examples 8–11 are tertiary etheramines having the chemical structure represented above in which $R_1$ is $C_{12}$–$C_{14}$ alkyl, m is 2, $R_2$ is isopropylene and $R_3$ is ethylene. The value of x+y is varied as shown in the table below.

Aqueous concentrate compositions containing 31% glyphosate a.e. in the form of the isopropylamine salt and 11% surfactant were prepared by a procedure similar to that of Examples 1–4. Cloud point of each composition was determined as shown in the table below.

| Example | x + y | Cloud point (°C.) |
|---------|-------|-------------------|
| 8 | 2 | 76 |
| 9 | 5 | >95 |
| 10 | 10 | >95 |
| 11 | 15 | 71 |

Example 12

Comparative herbicidal efficacy was determined in a field test at Jerseyville, Ill. Treatments were applied post-emergence to plants which had grown from seeds planted mechanically in rows. A randomized block design with three replicates was used. Applications were made with a backpack sprayer with multiple nozzles giving an overlapping spray pattern to maximize uniformity of application. Herbicidal efficacy was evaluated as percent control estimated visually by comparison with untreated plots.

Plant species on which herbicidal efficacy was evaluated were Japanese millet (*Echinochloa crus-galli*, ECHCF), broadleaf signalgrass (*Brachiaria platyphylla*, BRAPP), prickly sida (*Sida spinosa*, SIDSP), redroot pigweed (*Amaranthus retroflexus*, AMARE), hemp sesbania (*Sesbania exaltata*, SEBEX), morningglory (*Ipomoea sp.*, IPOSS) and velvetleaf (*Abutilon theophrasti*, ABUTH).

All glyphosate formulations in this test were aqueous concentrates diluted in water to give an application volume of 93 l/ha. Dilutions were made so as to give three glyphosate application rates of 314, 628 and 840 g a.e./ha for each formulation.

Standard treatments used for reference in this field test were made with concentrate formulations A and B containing glyphosate isopropylamine salt at 360 g a.e./l and respectively 15.4% and 7.7% of MON 0818, a surfactant based on ethoxylated tallowamine having an average of 15 moles of EO.

Concentrate formulations C–J of the invention contained glyphosate in the form of the isopropylamine salt at 360 g a.e./l. Concentrate formulations C–F further contained, as sole surfactant, a tertiary etheramine having the chemical structure represented above in which $R_1$ is $C_{12}$–$C_{14}$ alkyl, m is 2, x+y is 5, $R_2$ is isopropylene and $R_3$ is ethylene. Surfactant contents in concentrate formulations C, D, E and F were respectively 3.5%, 5.5%, 7.5% and 10%. Concentrate formulations D and F are essentially identical to the compositions of Examples 4 and 3 above, respectively. Concentrate formulations G–J contained, as sole surfactant, a tertiary etheramine having the chemical structure represented above in which $R_1$ is $C_{12}$–$C_{14}$ alkyl, m is 3, x+y is 5, and $R_2$ and $R_3$ are each ethylene. Surfactant contents in concentrate formulations G, H, I and J were, respectively, 3.5%, 5.5%, 7.5% and 10%. Concentrate formulations H and J are essentially identical to the compositions of Examples 2 and 1 above respectively.

Concentrate formulations K and L of the invention contained glyphosate in the form of the isopropylamine salt at 420 g a.e./l and a tertiary etheramine surfactant having the chemical structure represented above in which $R_1$ is $C_{12}$–$C_{14}$ alkyl, m is 3, x+y is 5, and $R_2$ and $R_3$ are each ethylene. Etheramine surfactant contents in concentrate formulations K and L were respectively 5.5% and 3.5%. Concentrate formulation L additionally contained 3.9% of an alkyl polyglucoside surfactant having a $C_9$–$C_{11}$ alkyl chain and an alkyl/glucose molar ratio of 1:1.6.

Results of the field test are tabulated below.

| Formulation | g a.e./ha | Percent control ||||||| 
|---|---|---|---|---|---|---|---|---|
| | | ECHCF | BRAPP | SIDSP | AMARE | SEBEX | IPOSS | ABUTH |
| A | 314 | 97 | 96 | 70 | 96 | 99 | 59 | 59 |
| B | 314 | 97 | 98 | 81 | 95 | 98 | 52 | 52 |
| C | 314 | 100 | 100 | 68 | 98 | 100 | 49 | 50 |
| D | 314 | 98 | 98 | 73 | 96 | 100 | 48 | 50 |
| E | 314 | 100 | 100 | 52 | 95 | 100 | 46 | 50 |
| F | 314 | 100 | 100 | 75 | 96 | 100 | 58 | 59 |
| G | 314 | 100 | 100 | 66 | 94 | 99 | 53 | 52 |
| H | 314 | 99 | 100 | 50 | 88 | 98 | 53 | 55 |
| I | 314 | 97 | 98 | 65 | 97 | 97 | 60 | 63 |
| J | 314 | 98 | 100 | 74 | 95 | 97 | 60 | 56 |
| K | 314 | 92 | 96 | 76 | 93 | 98 | 54 | 53 |
| L | 314 | 97 | 98 | 77 | 95 | 97 | 55 | 56 |
| A | 628 | 100 | 100 | 96 | 100 | 100 | 73 | 75 |
| B | 628 | 100 | 100 | 95 | 99 | 99 | 68 | 66 |
| C | 628 | 100 | 100 | 94 | 99 | 100 | 71 | 70 |
| D | 628 | 100 | 98 | 95 | 100 | 100 | 85 | 78 |
| E | 628 | 100 | 100 | 98 | 99 | 99 | 77 | 77 |
| F | 628 | 100 | 100 | 93 | 100 | 100 | 81 | 79 |
| G | 628 | 100 | 100 | 99 | 99 | 100 | 87 | 84 |
| H | 628 | 100 | 100 | 97 | 98 | 100 | 74 | 72 |
| I | 628 | 100 | 100 | 97 | 100 | 100 | 83 | 78 |
| J | 628 | 100 | 100 | 98 | 99 | 100 | 77 | 70 |
| K | 628 | 100 | 98 | 92 | 99 | 99 | 72 | 73 |
| L | 628 | 100 | 100 | 94 | 99 | 100 | 79 | 81 |
| A | 840 | 100 | 100 | 97 | 99 | 100 | 90 | 78 |
| B | 840 | 100 | 100 | 99 | 99 | 100 | 87 | 81 |
| C | 840 | 100 | 100 | 100 | 100 | 100 | 90 | 90 |
| D | 840 | 100 | 98 | 100 | 100 | 100 | 89 | 83 |
| E | 840 | 100 | 100 | 98 | 100 | 100 | 91 | 86 |
| F | 840 | 100 | 100 | 99 | 99 | 100 | 90 | 88 |
| G | 840 | 100 | 100 | 96 | 100 | 100 | 86 | 83 |

-continued

| Formulation | g a.e./ha | ECHCF | BRAPP | SIDSP | AMARE | SEBEX | IPOSS | ABUTH |
|---|---|---|---|---|---|---|---|---|
| | | | | Percent control | | | | |
| H | 840 | 100 | 100 | 100 | 100 | 100 | 86 | 83 |
| I | 840 | 100 | 100 | 96 | 98 | 100 | 88 | 80 |
| J | 840 | 100 | 100 | 98 | 100 | 100 | 92 | 82 |
| K | 840 | 100 | 100 | 100 | 100 | 100 | 92 | 92 |
| L | 840 | 100 | 100 | 99 | 99 | 99 | 88 | 86 |

Example 13

The surfactant used in Example 13 is the same as that used in Example 1. The dry water-soluble granular composition of Example 13 was prepared by adding to a small food-processor bowl the following ingredients:

(1) powdered ammonium glyphosate containing 86.6% glyphosate a.e., 37.5 g.

(2) surfactant as defined above, 12.5 g.

(3) water, 2.5 g.

No gelling of the surfactant was observed. The ingredients were mixed, forming homogeneous small granules. The granules were dried in a fluid-bed dryer at 65° C. for 15 minutes.

The composition can be calculated to contain, on a dry weight basis, 25% surfactant. Glyphosate assay was determined to be 61.8% a.e.

Example 14

The surfactant used in Example 14 is the same as that used in Example 3. The dry water-soluble granular composition of Example 14 was prepared by adding to a small food-processor bowl the following ingredients:

(1) powdered ammonium glyphosate containing 86.6% glyphosate a.e., 37.5 g.

(2) surfactant as defined above, 12.5 g.

(3) water, 2.5 g.

No gelling of the surfactant was observed. The ingredients were mixed, forming homogeneous small granules. The granules were dried in a fluid-bed dryer at 65° C. for 15 minutes.

The composition can be calculated to contain, on a dry weight basis, 25% surfactant. Glyphosate assay was determined to be 66.2% a.e.

Example 15

For comparative greenhouse testing of herbicidal efficacy, aqueous concentrate compositions containing 31% glyphosate a.e. in the form of the isopropylamine salt and 5.5% surfactant were prepared by a procedure similar to that of Examples 1–4.

Formulations C1 and C2 were made using tertiary alkylamine surfactants of prior art. The surfactant in C1 is an ethoxylated cocoamine having 5 moles of EO. If the representative chemical structure shown for a tertiary etheramine of the invention is applied to the surfactant of C1, it will be seen that $R_1$ is coco alkyl of average carbon chain length about 12, m is 0, $R_3$ is ethylene and x+y is 5. The surfactant in C2 is an ethoxylated tallowamine having 5 moles of EO. If the representative chemical structure shown for a tertiary etheramine of the invention is applied to the surfactant of C2, it will be seen that $R_1$ is tallow alkyl of average carbon chain length about 18, m is 0, $R_3$ is ethylene and x+y is 5.

Formulations E1–E9 were made using tertiary or quaternary N-methyl etheramine surfactants of the invention. The chemical structures of these surfactants can be deduced from the following table, by reference to the representative structures shown above.

| Formulation | Surfactant type | $R_1$ | $R_2$ | $R_3$ | m | x + y | $A^-$ |
|---|---|---|---|---|---|---|---|
| E1 | tertiary | $C_{12-14}$ alkyl | $CH_2CH(CH_3)$ | $CH_2CH_2$ | 2 | 5 | |
| E2 | tertiary | coco alkyl | $CH_2CH_2CH_2$ | $CH_2CH_2$ | 1 | 10 | |
| E3 | tertiary | isodecyl | $CH_2CH_2CH_2$ | $CH_2CH_2$ | 1 | 2 | |
| E4 | tertiary | isodecyl | $CH_2CH_2CH_2$ | $CH_2CH_2$ | 1 | 5 | |
| E5 | tertiary | isotridecyl | $CH_2CH_2CH_2$ | $CH_2CH_2$ | 1 | 2 | |
| E6 | tertiary | isotridecyl | $CH_2CH_2CH_2$ | $CH_2CH_2$ | 1 | 5 | |
| E7 | tertiary | $C_{15}$ alkyl | $CH_2CH_2CH_2$ | $CH_2CH_2$ | 1 | 2 | |
| E8 | quaternary | isodecyl | $CH_2CH_2CH_2$ | $CH_2CH_2$ | 1 | 2 | $Cl^-$ |
| E9 | quaternary | isotridecyl | $CH_2CH_2CH_2$ | $CH_2CH_2$ | 1 | 2 | $Cl^-$ |

For greenhouse testing, seeds of velvetleaf (*Abutilon theophrasti*, ABUTH) and Japanese millet (*Echinochloa crus-galli*, ECHCF) were planted in 10.2 cm square pots of soil with added fertilizer. Plants were allowed to grow until the desired growth stage or size (3-leaf stage for ABUTH, 20–25 cm height for ECHCF) for spraying. Pots were selected for uniformity before treatment and four replicate pots were assigned to each treatment, including an untreated control. Spray solutions were prepared by dilution of the concentrate glyphosate formulations in water. Spraying was performed with a device which simulates agricultural field spraying equipment, delivering a fine spray at a pressure of about 207 kilopascals. Speed of travel of the spray device over the plants was adjusted to give the desired spray volume of 187 l/ha. For logistical reasons, all four replicates of each treatment were sprayed together. After spraying, the plants were returned to the greenhouse. Herbicidal efficacy was evaluated by visual assessment 16 days after treatment and recorded as "percent control" on an arbitrary scale by comparison with untreated plants. On this scale 0 means no visible effect and 100 means death of all plants. In the table below, percent control values given are the means of four replicates.

| g a.e./ha: | Percent control | | | | | | | |
|---|---|---|---|---|---|---|---|---|
| | ABUTH | | | | ECHCF | | | |
| Formulation | 112 | 224 | 336 | 448 | 112 | 224 | 336 | 448 |
| C1 | 0 | 1 | 60 | 50 | 6 | 30 | 61 | 50 |
| C2 | 0 | 6 | 53 | 79 | 0 | 6 | 53 | 79 |
| E1 | 1 | 13 | 58 | 78 | 10 | 55 | 78 | 86 |
| E2 | 3 | 15 | 49 | 65 | 3 | 15 | 49 | 91 |
| E3 | 0 | 9 | 50 | 60 | 9 | 53 | 69 | 89 |
| E4 | 0 | 4 | 35 | 65 | 10 | 53 | 55 | 78 |
| E5 | 0 | 0 | n.d. | 53 | 5 | 50 | n.d. | 95 |
| E6 | 0 | 6 | 55 | 65 | 15 | 55 | 71 | 81 |
| E7 | 0 | 5 | 50 | 71 | 6 | 55 | 75 | 86 |
| E8 | 0 | 5 | 40 | 73 | 10 | 61 | 76 | 97 |
| E9 | 3 | 13 | 71 | 70 | 5 | 58 | 73 | 75 | n.d. = no data

Example 16

To determine compatibility of surfactants of the invention with very concentrated aqueous formulations of glyphosate, aqueous concentrate compositions containing 480 g/l glyphosate a.e. in the form of the isopropylamine salt and 80 g/l surfactant were prepared by a procedure similar to that of Examples 1–4. The compositions of Example 16 are approximately one-third more concentrated in respect of glyphosate a.e. than those of Example 15.

Formulations C3 and C4 were made using tertiary alkylamine surfactants of prior art. The surfactant in C3 is the same as that in formulation C1 of Example 15. The surfactant in C4 is the same as that in formulation C2 of Example 15.

Formulations E10, E11, E12 and E13 were made using the same tertiary or quaternary N-methyl etheramine surfactants of the invention as are present in formulations E1, E6, E8 and E9 respectively of Example 15.

Surfactant compatibility was determined by measuring cloud point of the formulations, as shown in the table below.

| Formulation | Cloud point (°C.) |
|---|---|
| C3 | >90 |
| C4 | >90 |
| E10 | >90 |
| E11 | >90 |
| E12 | >90 |
| E13 | >90 |

Example 17

Compositions of the invention were prepared by a procedure similar to that of Examples 1–4 to illustrate the incorporation of a nonionic surfactant together with the etheramine surfactant in a highly concentrated aqueous glyphosate formulation. In formulations E14–E25 glyphosate is present as its isopropylamine salt at 480 g a.e./l and the total surfactant (etheramine plus nonionic surfactant) concentration is 80 g/l. In all cases the weight/weight ratio of etheramine to the nonionic surfactant is 4:1.

The etheramine surfactant in formulation E14 is the same as that in formulation E1 of Example 15. The nonionic surfactant in formulation E14 is an ethoxylated $C_{14}$–$C_{16}$ linear primary alcohol having an average of 7 moles of EO.

The etheramine surfactant in formulation E15 is the same as that in formulation E1 of Example 15. The nonionic surfactant in formulation E15 is an ethoxylated $C_{12}$–$C_{13}$ linear primary alcohol having an average of 5 moles of EO.

The etheramine surfactant in formulation E16 is the same as that in formulation E1 of Example 15. The nonionic surfactant in formulation E16 is an ethoxylated $C_{11}$ linear primary alcohol having an average of 7 moles of EO.

The etheramine surfactant in formulation E17 is the same as that in formulation E1 of Example 15. The nonionic surfactant in formulation E17 is an ethoxylated $C_{11}$–$C_{12}$ linear primary alcohol having an average of 6 moles of EO.

The etheramine surfactant in formulation E18 is the same as that in formulation E1 of Example 15. The nonionic surfactant in formulation E18 is an ethoxylated $C_{12}$–$C_{15}$ secondary alcohol having an average of 9 moles of EO.

The etheramine surfactant in formulation E19 is the same as that in formulation E1 of Example 15. The nonionic surfactant in formulation E19 is an alkyl polyglucoside having a $C_8$–$C_{10}$ alkyl chain and an average of 1.7 moles of glucose.

The etheramine surfactant in formulation E20 is the same as that in formulation E6 of Example 15. The nonionic surfactant in formulation E20 is an ethoxylated $C_{14}$–$C_{16}$ linear primary alcohol having an average of 7 moles of EO.

The etheramine surfactant in formulation E21 is the same as that in formulation E6 of Example 15. The nonionic surfactant in formulation E21 is an ethoxylated $C_{12}$–$C_{15}$ secondary alcohol having an average of 9 moles of EO.

The etheramine surfactant in formulation E22 is the same as that in formulation E8 of Example 15. The nonionic surfactant in formulation E22 is an ethoxylated $C_{14}$–$C_{16}$ linear primary alcohol having an average of 7 moles of EO.

The etheramine surfactant in formulation E23 is the same as that in formulation E8 of Example 15. The nonionic surfactant in formulation E23 is an ethoxylated $C_{12}$–$C_{15}$ secondary alcohol having an average of 9 moles of EO.

The etheramine surfactant in formulation E24 is the same as that in formulation E9 of Example 15. The nonionic surfactant in formulation E24 is an ethoxylated $C_{14}$–$C_{16}$ linear primary alcohol having an average of 7 moles of EO.

The etheramine surfactant in formulation E25 is the same as that in formulation E9 of Example 15. The nonionic surfactant in formulation E25 is an ethoxylated $C_{12}$–$C_{15}$ secondary alcohol having an average of 9 moles of EO.

Cloud points of formulations E14–E25 are shown in the table below.

| Formulation | Cloud point (°C.) |
|---|---|
| E14 | 79 |
| E15 | 73 |
| E16 | 63 |
| E17 | 71 |
| E18 | 77 |
| E19 | >90 |
| E20 | >90 |
| E21 | >90 |
| E22 | >90 |
| E23 | >90 |
| E24 | >90 |
| E25 | >90 |

An attempt was made to make formulations similar to E14–E25, but containing, in place of the etheramine component, an ethoxylated tertiary alkylamine surfactant of prior art. Whether a cocoamine with 5 moles of EO or a tallowamine with 5 moles of EO was used, the prior art surfactant was found to be incompatible with any of the ethoxylated primary or secondary alcohol surfactants used in formulations E14–E25, at equal glyphosate, amine surfactant and nonionic surfactant loadings as in these same formulations. Thus, a further unexpected advantage of etheramine surfactants of the present invention over alkylamine surfactants of prior art is their relatively good compatibility with nonionic surfactants in highly concentrated aqueous glyphosate formulations.

While the illustrative embodiments of the invention have been described with particularity, it will be understood that various other modifications will be apparent to and can be readily made by those skilled in the art without departing from the spirit and scope of the invention. Accordingly, it is not intended that the scope of the claims appended hereto be limited to the examples and descriptions set forth hereinabove but rather that the claims be construed as encompassing all the features of patentable novelty which reside in the present invention, including all features which would be treated as equivalents thereof by those skilled in the art to which the invention pertains.

Example 18

Further to the compositions of Example 15, aqueous concentrate compositions containing 31% glyphosate a.e. in the form of the isopropylamine salt and 5.5% surfactant were prepared by a procedure similar to that of Examples 1–4.

Formulations C1 and C2 are as in Example 15.

Formulations C3 and C4 were likewise made using tertiary alkylamine surfactants of prior art. The surfactant in C3 is an ethoxylated cocoamine having 2 moles of EO. The surfactant in C4 is an ethoxylated tallowamine having 2 moles of EO.

Formulation C5 was made using a quaternary alkylamine surfactant of prior art, which is N-methyl cocoammonium chloride having 2 moles of EO.

Formulation C6 was made using an alkylamine oxide surfactant of prior art, supplied by Tomah Products, Inc. as "AO-728 Special". It is an alkylamine N-oxide having 2 moles of EO; the chain length or origin of the alkyl chain is not disclosed by Tomah.

Formulations E1–E9 are as in Example 15.

Formulation E26 was made using an etheramine oxide surfactant of the invention. Its chemical structure can be deduced from the following table, by reference to the representative structures shown above.

| Formulation | Surfactant type | $R_1$ | $R_2$ | $R_3$ | m | x + y | $A^-$ |
|---|---|---|---|---|---|---|---|
| E26 | N-oxide | isodecyl | $CH_2CH(CH_3)$ | $CH_2CH_2$ | 1 | 2 | |

Greenhouse testing was conducted exactly as described in Example 15, except that herbicidal efficacy was evaluated 17 days after treatment. Average percent control is shown in the table below.

| | Percent control | | | | | | | |
|---|---|---|---|---|---|---|---|---|
| g a.e./ha: | ABUTH | | | | ECHCF | | | |
| Formulation | 224 | 336 | 448 | 672 | 224 | 336 | 448 | 672 |
| C1 | 33 | 58 | 69 | 83 | 41 | 69 | 66 | 95 |
| C2 | 44 | 58 | 74 | 78 | 39 | 60 | 63 | 95 |
| C3 | 44 | 49 | 85 | 84 | 50 | 64 | 83 | 81 |
| C4 | 41 | 51 | 65 | 85 | 54 | 66 | 84 | 88 |
| C5 | 31 | 41 | 66 | 76 | 51 | 71 | 86 | 96 |
| C6 | 34 | 38 | 60 | 69 | 46 | 64 | 65 | 81 |
| E1 | 46 | 65 | 83 | 91 | 48 | 71 | 91 | 99 |
| E2 | 50 | 59 | 75 | 85 | 40 | 60 | 71 | 93 |
| E3 | 46 | 56 | 68 | 73 | 39 | 55 | 66 | 95 |
| E4 | 39 | 55 | 78 | 80 | 49 | 59 | 79 | 89 |
| E5 | 40 | 51 | 73 | 75 | 51 | 63 | 79 | 89 |
| E6 | 49 | 60 | 83 | 86 | 51 | 63 | 80 | 90 |
| E7 | 31 | 39 | 75 | 75 | 46 | 63 | 75 | 95 |
| E8 | 43 | 55 | 73 | 80 | 46 | 58 | 73 | 93 |
| E9 | 48 | 50 | 84 | 85 | 51 | 60 | 85 | 98 |
| E26 | 48 | 59 | 73 | 83 | 48 | 61 | 84 | 94 |

While the illustrative embodiments of the invention have been described with particularity, it will be understood that various other modifications will be apparent to and can be readily made by those skilled in the art without departing from the spirit and scope of the invention. Accordingly, it is not intended that the scope of the claims appended hereto be limited to the examples and descriptions set forth hereinabove but rather that the claims be construed as encompassing all the features of patentable novelty which reside in the present invention, including all features which would be treated as equivalents thereof by those skilled in the art to which the invention pertains.

What is claimed is:

1. A herbicidal composition comprising
   (a) a herbicidally effective amount of glyphosate or a salt thereof; and
   (b) an effective herbicidal activity enhancing amount of a surfactant having the chemical structure

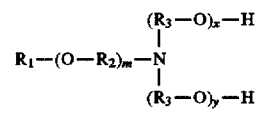

wherein $R_1$ is a straight or branched chain $C_6$ to about $C_{22}$ alkyl, aryl or alkylaryl group, m is an average number from 1 to about 10, $R_2$ in each of the m ($O$—$R_2$) groups is independently $C_1$–$C_4$ alkylene, $R_3$ groups are independently $C_1$–$C_4$ alkylene, and x and y are average numbers such that x+y is in the range from 2 to about 60.

2. A herbicidal composition comprising
   (a) a herbicidally effective amount of glyphosate or a salt thereof; and
   (b) an effective herbicidal activity enhancing amount of a surfactant having the chemical structure

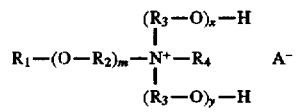

wherein $R_1$ is a straight or branched chain $C_6$ to about $C_{22}$ alkyl, aryl or alkylaryl group, m is an average number from 1 to about 10, $R_2$ in each of the m ($O$—$R_2$) groups is independently $C_1$–$C_4$ alkylene, $R_3$ groups are independently $C_1$–$C_4$ alkylene, $R_4$ is $C_1$–$C_4$ alkyl, x and y are average numbers such that x+y is in the range from 0 to about 60, and $A^-$ is an agriculturally acceptable anion.

3. A herbicidal composition comprising
 (a) a herbicidally effective amount of glyphosate or a salt thereof; and
 (b) an effective herbicidal activity enhancing amount of a surfactant having the chemical structure

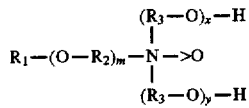

wherein $R_1$ is a straight or branched chain $C_6$ to about $C_{22}$ alkyl, aryl or alkylaryl group, m is an average number from 1 to about 10, $R_2$ in each of the m (O—$R_2$) groups is independently $C_1$–$C_4$ alkylene, $R_3$ groups are independently $C_1$–$C_4$ alkylene, and x and y are average numbers such that x+y is in the range from 2 to about 60.

4. A herbicidal composition in the form of a spray solution prepared on site by tank-mixing
 (a) a herbicidally effective amount of a composition comprising glyphosate or a salt thereof;
 (b) an effective herbicidal activity enhancing amount of a composition comprising a surfactant having the chemical structure

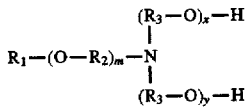

wherein $R_1$ is a straight or branched chain $C_6$ to about $C_{22}$ alkyl, aryl or alkylaryl group, m is an average number from 1 to about 10, $R_2$ in each of the m (O—$R_2$) groups is independently $C_1$–$C_4$ alkylene, $R_3$ groups are independently $C_1$–$C_4$ alkylene, and x and y are average numbers such that x+y is in the range from 2 to about 60; and
 (c) water.

5. A herbicidal composition in the form of a spray solution prepared on site by tank-mixing
 (a) a herbicidally effective amount of a composition comprising glyphosate or a salt thereof;
 (b) an effective herbicidal activity enhancing amount of a composition comprising a surfactant having the chemical structure

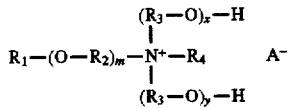

wherein $R_1$ is a straight or branched chain $C_6$ to about $C_{22}$ alkyl, aryl or alkylaryl group, m is an average number from 1 to about 10, $R_2$ in each of the m (O—$R_2$) groups is independently $C_1$–$C_4$ alkylene, $R_3$ groups are independently $C_1$–$C_4$ alkylene, $R_4$ is $C_1$–$C_4$ alkyl, x and y are average numbers such that x+y is in the range from 0 to about 60, and $A^-$ is an agriculturally acceptable anion; and
 (c) water.

6. A herbicidal composition in the form of a spray solution prepared on site by tank-mixing
 (a) a herbicidally effective amount of a composition comprising glyphosate or a salt thereof;
 (b) an effective herbicidal activity enhancing amount of a composition comprising a surfactant having the chemical structure

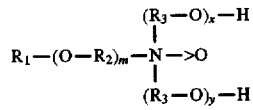

wherein $R_1$ is a straight or branched chain $C_6$ to about $C_{22}$ alkyl, aryl or alkylaryl group, m is an average number from 1 to about 10, $R_2$ in each of the m (O—$R_2$) groups is independently $C_1$–$C_4$ alkylene, $R_3$ groups are independently $C_1$–$C_4$ alkylene, and x and y are average numbers such that x+y is in the range from 2 to about 60; and
 (c) water.

7. A herbicidal composition of claim 1, 2 or 3 wherein the glyphosate or salt thereof and the surfactant are dissolved in water and the composition is ready to use.

8. A herbicidal composition of claim 7 wherein the glyphosate or salt thereof is present at about 1 to about 50 g a.e./l.

9. A herbicidal composition of claim 8 wherein the glyphosate or salt thereof is present at about 5 to about 20 g a.e./l.

10. A herbicidal composition of claim 7 wherein said surfactant is present at about 0.125% to about 2% weight/volume.

11. A herbicidal composition of claim 1 wherein the glyphosate or salt thereof is present at about 5 to about 20 g a.e./l; the surfactant is present at about 0.125% to about 2% weight/volume; the glyphosate or salt thereof and the surfactant are dissolved in water and the composition is ready to use; and, in the chemical structure of said surfactant, $R_1$ is $C_8$–$C_8$ alkyl, $R_2$ is linear propylene, isopropylene or ethylene, $R_3$ is ethylene, m is in the range from 1 to about 5 and x+y is in the range from 2 to about 20.

12. A herbicidal composition of claim 11 wherein, in the chemical structure of said surfactant, $R_2$ is isopropylene or ethylene.

13. A herbicidal composition of claim 11 wherein, in the chemical structure of said surfactant, $R_2$ is linear propylene and m is 1.

14. A herbicidal composition of claim 2 wherein the glyphosate or salt thereof is present at about 5 to about 20 g a.e./l; the surfactant is present at about 0.125% to about 2% weight/volume; the glyphosate or salt thereof and the surfactant are dissolved in water and the composition is ready to use; and, in the chemical structure of said surfactant, $R_1$ is $C_8$–$C_{18}$ alkyl, $R_2$ is linear propylene, isopropylene or ethylene, $R_3$ is ethylene, $R_4$ is methyl, m is in the range from 1 to about 5, x+y is in the range from 0 to about 20, and $A^-$ is an anion selected from the group consisting of halide, phosphate and sulfate.

15. A herbicidal composition of claim 14 wherein, in the chemical structure of said surfactant, $R_2$ is linear propylene and m is 1.

16. A liquid concentrate herbicidal composition of claim 1, 2 or 3 which further comprises water and wherein the glyphosate or salt thereof is present at about 50 to about 500 g a.e./l.

17. A herbicidal composition of claim 16 wherein the glyphosate or salt thereof is present at about 200 to about 500 g a.e./l.

18. A herbicidal composition of claim 17 wherein the glyphosate or salt thereof is present at about 350 to about 500 g a.e./l.

19. A herbicidal composition of claim 18 wherein the glyphosate or salt thereof is present at about 450 to about 500 g a.e./l.

20. A herbicidal composition of claim 16 wherein the glyphosate is present as a salt selected from the group consisting of the ammonium, alkylamine, alkanolamine, alkylsulfonium and alkali metal salts of glyphosate.

21. A herbicidal composition of claim 20 wherein the glyphosate is present as its isopropylamine salt.

22. A liquid concentrate herbicidal composition of claim 1 which further comprises water; wherein the glyphosate or salt thereof is present at about 50 to about 500 g a.e./l; and wherein, in the chemical structure of said surfactant, $R_1$ is $C_8$–$C_{18}$ alkyl, $R_2$ is linear propylene, isopropylene or ethylene, $R_3$ is ethylene, m is in the range from 1 to about 5 and x+y is in the range from about 2 to about 20.

23. A herbicidal composition of claim 22 wherein the weight/weight ratio of said surfactant to glyphosate a.e. is in the range from about 1:20 to about 1:1.

24. A herbicidal composition of claim 23 wherein the weight/weight ratio of said surfactant to glyphosate a.e. is in the range from about 1:10 to about 1:2.

25. A herbicidal composition of claim 22, 23 or 24 wherein, in the chemical structure of said surfactant, $R_2$ is isopropylene or ethylene.

26. A herbicidal composition of claim 25 wherein, in the chemical structure of said surfactant, $R_1$ is $C_{12}$–$C_{14}$ alkyl, $R_2$ is isopropylene, m is 2 and x+y is 5.

27. A herbicidal composition of claim 25 wherein, in the chemical structure of said surfactant, $R_1$ is $C_{12}$–$C_{14}$ alkyl, $R_2$ is ethylene, m is 3 and x+y is 5.

28. A herbicidal composition of claim 22, 23 or 24 wherein, in the chemical structure of said surfactant, $R_2$ is linear propylene and m is 1.

29. A herbicidal composition of claim 28 wherein, in the chemical structure of said surfactant, $R_1$ is a straight or branched chain alkyl group having from about 10 to about 15 carbon atoms, and x+y is in the range from 2 to about 10.

30. A herbicidal composition of claim 29 wherein, in the chemical structure of said surfactant, x+y is in the range from 2 to about 5.

31. A liquid concentrate herbicidal composition of claim 2 which further comprises water; wherein the glyphosate or salt thereof is present at about 50 to about 500 g a.e./l; and wherein, in the chemical structure of said surfactant, $R_1$ is $C_8$–$C_{18}$ alkyl, $R_2$ is linear propylene, isopropylene or ethylene, $R_3$ is ethylene, $R_4$ is methyl, m is in the range from 1 to about 5, x+y is in the range from about 0 to about 20, and $A^-$ is an anion selected from the group consisting of halide, phosphate and sulfate.

32. A herbicidal composition of claim 31 wherein the weight/weight ratio of said surfactant to glyphosate a.e. is in the range from about 1:20 to about 1:1.

33. A herbicidal composition of claim 32 wherein the weight/weight ratio of said surfactant to glyphosate a.e. is in the range from about 1:10 to about 1:2.

34. A herbicidal composition of any of claim 31, 32 or 33 wherein, in the chemical structure of said surfactant, $R_2$ is linear propylene and m is 1.

35. A herbicidal composition of claim 34 wherein, in the chemical structure of said surfactant, $R_1$ is a straight or branched chain alkyl group having from about 10 to about 15 carbon atoms, and x+y is in the range from 2 to about 10.

36. A herbicidal composition of claim 35 wherein, in the chemical structure of said surfactant, x+y is in the range from 2 to about 5.

37. A storage stable liquid concentrate herbicidal composition of either of claim 22 or claim 31 wherein (a) the glyphosate is present as its isopropylamine or trimethylsulfonium salt at a concentration in the range from about 450 to about 500 g a.e./l;

(b) the weight/weight ratio of glyphosate a.e. to total surfactant is in the range from about 5:1 to about 8:1; and (c) the etheramine surfactant comprises from about 75% to 100% by weight of the total surfactant present.

38. A herbicidal composition of claim 37 wherein (a) the glyphosate is present as its isopropylamine salt at a concentration of about 480 g a.e./l;

(b) total surfactant concentration is about 80 g/l;

(c) the etheramine surfactant comprises about 80% by weight of the total surfactant present;

(d) in the chemical structure of said etheramine surfactant, $R_1$ is a straight or branched chain alkyl group having from about 10 to about 15 carbon atoms, $R_2$ is isopropylene or ethylene, and x+y is in the range from 2 to about 5; and (e) the composition further comprises, at about 20% by weight of the total surfactant present, a nonionic surfactant.

39. A herbicidal composition of claim 37 wherein (a) the glyphosate is present as its isopropylamine salt at a concentration of about 480 g a.e./l;

(b) total surfactant concentration is about 80 g/l;

(c) the etheramine surfactant comprises about 80% by weight of the total surfactant present;

(d) in the chemical structure of said etheramine surfactant, $R_1$ is a straight or branched chain alkyl group having from about 10 to about 15 carbon atoms, $R_2$ is linear propylene, m is 1, and x+y is in the range from 2 to about 5; and (e) the composition further comprises, at about 20% by weight of the total surfactant present, a nonionic surfactant.

40. A dry concentrate herbicidal composition of claim 1, 2 or 3 wherein the glyphosate or salt thereof is present at about 20% to about 80% weight/weight.

41. A herbicidal composition of claim 40 wherein the glyphosate or salt thereof is present at about 50% to about 76% weight/weight.

42. A herbicidal composition of claim 41 wherein the glyphosate or salt thereof is present at about 60% to about 72% weight/weight.

43. A herbicidal composition of claim 40 wherein the glyphosate is present as a salt selected from the group consisting of the ammonium, alkylamine, alkanolamine, alkylsulfonium and alkali metal salts of glyphosate.

44. A herbicidal composition of claim 43 wherein the glyphosate is present as its ammonium salt.

45. A dry concentrate herbicidal composition of claim 1 wherein the glyphosate or salt thereof is present at about 20% to about 80% weight/weight; and wherein, in the chemical structure of said surfactant, $R_1$ is $C_8$–$C_{18}$ alkyl, $R_2$ is linear propylene, isopropylene or ethylene, $R_3$ is ethylene, m is in the range from 1 to about 5 and x+y is in the range from about 2 to about 20.

46. A herbicidal composition of claim 45 wherein the weight/weight ratio of said surfactant to glyphosate a.e. is in the range from about 1:20 to about 1:1.

47. A herbicidal composition of claim 46 wherein the weight/weight ratio of said surfactant to glyphosate a.e. is in the range from about 1:10 to about 1:2.

48. A herbicidal composition of claim 45, 46 or 47 wherein, in the chemical structure of said surfactant, $R_2$ is isopropylene or ethylene.

49. A herbicidal composition of claim 48 wherein, in the chemical structure of said surfactant, $R_1$ is $C_{12}$–$C_{14}$ alkyl, $R_2$ is isopropylene, m is 2 and x+y is 5.

50. A herbicidal composition of claim 48 wherein, in the chemical structure of said surfactant, $R_1$ is $C_{12}$–$C_{14}$ alkyl, $R_2$ is ethylene, m is 3 and x+y is 5.

51. A herbicidal composition of claim 45, 46 or 47 wherein, in the chemical structure of said surfactant, $R_2$ is linear propylene and m is 1.

52. A herbicidal composition of claim 51 wherein, in the chemical structure of said surfactant, $R_1$ is a straight or branched chain alkyl group having from about 10 to about 15 carbon atoms, and x+y is in the range from 2 to about 10.

53. A herbicidal composition of claim 52 wherein, in the chemical structure of said surfactant, x+y is in the range from 2 to about 5.

54. A dry concentrate herbicidal composition of claim 2 wherein the glyphosate or salt thereof is present at about 20% to about 80% weight/weight; and wherein, in the chemical structure of said surfactant, $R_1$ is $C_8$–$C_{18}$ alkyl, $R_2$ is linear propylene, isopropylene or ethylene, $R_3$ is ethylene, $R_4$ is methyl, m is in the range from 1 to about 5, x+y is in the range from about 0 to about 20, and $A^-$ is an anion selected from the group consisting of halide, phosphate and sulfate.

55. A herbicidal composition of claim 54 wherein the weight/weight ratio of said surfactant to glyphosate a.e. is in the range from about 1:20 to about 1:1.

56. A herbicidal composition of claim 55 wherein the weight/weight ratio of said surfactant to glyphosate a.e. is in the range from about 1:10 to about 1:2.

57. A herbicidal composition of any of claims 54-56 wherein, in the chemical structure of said surfactant, $R_2$ is linear propylene and m is 1.

58. A herbicidal composition of claim 57 wherein, in the chemical structure of said surfactant, $R_1$ is a straight or branched chain alkyl group having from about 10 to about 15 carbon atoms, and x+y is in the range from 2 to about 10.

59. A herbicidal composition of claim 58 wherein, in the chemical structure of said surfactant, x+y is in the range from 2 to about 5.

60. A method of killing or controlling weeds or unwanted vegetation comprising the steps of (a) diluting a composition of claim 16 in a convenient amount of water to form a spray solution; and (b) applying a herbicidally effective amount of the spray solution to the foliage of the weeds or unwanted vegetation.

61. A method of killing or controlling weeds or unwanted vegetation comprising the steps of (a) dissolving or dispersing a composition of claim 40 in a convenient amount of water to form a spray solution; and (b) applying a herbicidally effective amount of the spray solution to the foliage of the weeds or unwanted vegetation.

* * * * *

UNITED STATES PATENT AND TRADEMARK OFFICE
CERTIFICATE OF CORRECTION

PATENT NO. : 5,750,468
DATED : MAY 12, 1998
INVENTOR(S) : Daniel R. Wright/Ronald J. Brinker, Joseph J. Sandbrink/Al S. Wideman It is certified that error appears in the above-identified patent and that said Letters Patent is hereby corrected as shown below:

In claim 11, line 35, please delete "$C_8$-$C_8$" and insert therefor --$C_8$-$C_{18}$--.

Signed and Sealed this

Eighth Day of September, 1998

Attest:

BRUCE LEHMAN

*Attesting Officer*     *Commissioner of Patents and Trademarks*